United States Patent [19]
Lion et al.

[11] Patent Number: 6,093,384
[45] Date of Patent: Jul. 25, 2000

[54] HAIR-CARE COMPOSITION COMPRISING AN AQUEOUS POLYMER DISPERSION

[75] Inventors: Bertrand Lion, Livry Gargan; Jean Mondet, Aulnay Sous Bois, both of France

[73] Assignee: L'Oreal, Paris, France

[21] Appl. No.: 08/797,271

[22] Filed: Feb. 7, 1997

Related U.S. Application Data

[63] Continuation of application No. 08/478,021, Jun. 7, 1995, abandoned.

[30] Foreign Application Priority Data

Jun. 17, 1994 [FR] France ................................ 94 07479

[51] Int. Cl.[7] ........................................... A61K 9/12
[52] U.S. Cl. ........................... 424/45; 424/47; 424/70.11
[58] Field of Search ....................... 424/45, 47, DIG. 1, 424/DIG. 2, 70.11, 489; 514/957

[56] References Cited

U.S. PATENT DOCUMENTS

| | | |
|---|---|---|
| 4,198,330 | 4/1980 | Kaizerman et al. . |
| 4,300,580 | 11/1981 | O'Neill et al. . |
| 4,946,932 | 8/1990 | Jenkins . |
| 5,126,126 | 6/1992 | Varaprath et al. .................. 424/DIG. 1 |
| 5,135,742 | 8/1992 | Halloran et al. ...................... 424/70.11 |
| 5,164,177 | 11/1992 | Bhatt et al. ................................ 424/47 |
| 5,254,542 | 10/1993 | Sakuta et al. . |
| 5,523,365 | 6/1996 | Geck et al. .............................. 526/194 |

FOREIGN PATENT DOCUMENTS

| | | |
|---|---|---|
| 0 297 576 | 1/1989 | European Pat. Off. . |
| 0 309 114 | 3/1989 | European Pat. Off. . |
| 0 353 896 | 2/1990 | European Pat. Off. . |
| 0 478 284 | 4/1992 | European Pat. Off. . |
| 551748 | 7/1993 | European Pat. Off. . |
| 2 680 684 | 3/1993 | France . |
| 2 238 242 | 5/1991 | United Kingdom . |

OTHER PUBLICATIONS

Handt, C.M. (1987). Hair Fixatives. *Soap Cosmetics, Chemical Specialties*, vol. 63, No. 10, pp. 36;38;39;72 and 73.

Starch, M.S. (1984). *Drug & Cosmetic Industry.*, vol. 134, No. 6, pp. 38–44 and 102.

Martino, G.T. et al. (1992). *Spray Technology & Marketing*, Mar. Issue, pp. 34–39.

Oteri, R. et al. Cosmetics & Toiletries, vol. 106, pp. 29–34, 1991.

Research Disclosure, "Hair Grooming Compositions", vol. 326, (1991) New York (USA), pp. 390–391.

Research Disclosure, "Fast Drying Aqueous Nail Polish", vol. 326, (1991) New York (USA), p. 395.

*Primary Examiner*—Thurman K. Page
*Assistant Examiner*—Raj Bawa
*Attorney, Agent, or Firm*—Finnegan, Henderson, Farabow, Garrett & Dunner, L.L.P.

[57] ABSTRACT

The present application relates to hair-care compositions comprising aqueous polymer dispersions as film-forming agent. These polymers are obtained by free-radical polymerization of a radical monomer in the interior and/or partially at the surface of already existing polymer particles of polyester type.

17 Claims, No Drawings

HAIR-CARE COMPOSITION COMPRISING AN AQUEOUS POLYMER DISPERSION

This application is a continuation of application Ser. No. 08/478,021, Jun. 7, 1995, now abandoned.

The present invention relates to a hair-care composition comprising as film-forming agent an aqueous polymer dispersion, and to the use of such a dispersion in a hair-care composition.

It is known to use aqueous polymer dispersions as film-forming agent in hair-care compositions. The properties of the aqueous dispersions thus obtained depend on the nature of the polymers, and thus of the monomers, from which they are prepared. However, it may be of advantage to be able to modify slightly these properties, for example by accentuating/optimizing a particularly advantageous property or by developing a new property which the said dispersion would not have on the basis of its inherent composition.

An object of the invention is to provide a hair-care composition comprising an aqueous dispersion of a polymer chosen from the group consisting of polyesters, polyesteramides and alkyds which has properties which are improved relative to the polyester, polyesteramide and/or alkyd dispersions of the prior art.

Another object of the invention is therefore a hair-care composition comprising an aqueous polymer dispersion consisting of particles resulting from the free-radical polymerization of at least one radical monomer in the interior and/or partially at the surface of already existing particles of at least one polymer chosen from the group consisting of polyesters, polyesteramides and alkyds. Still another object of the invention is the use of an aqueous polymer dispersion consisting of particles resulting from the free-radical polymerization of at least one radical monomer in the interior and/or partially at the surface of already existing particles of at least one polymer chosen from the group consisting of polyesters, polyesteramides and alkyds as film-forming agent in a hair-care composition.

In the rest of the present description, "polyester" is understood to mean any polymer, alone or as a mixture, chosen from the group consisting of polyesters, polyesteramides and alkyds.

It has been found that the use in hair-care compositions of aqueous dispersions according to the invention, i.e. of aqueous dispersions of hybrid polyester polymers, makes it possible to obtain a composition which has particular properties, properties which it is not possible to obtain by using, for example, a simple mixture of existing aqueous dispersions of polyester and of acrylic and/or vinyl polymer.

One advantage of the present invention is therefore to be able, on the basis of an already existing aqueous polymer dispersion, to develop and/or optimize certain particularly advantageous properties in a relatively controlled manner.

In preparing the hair-care composition according to the invention, an aqueous polyester dispersion is prepared first of all. This dispersion may be prepared by the person skilled in the art on the basis of their general technical knowledge, in particular as follows. When the polyester polymer is insoluble in water, it is possible to dissolve it in an organic solvent which is slightly soluble in water, to add water so as form an emulsion, then to evaporate the organic solvent so as to give an aqueous dispersion of the polyester polymer in water, having a solids content of approximately 30–50% by weight. When the polyester polymer is autodispersible in water, this step may be omitted if the polymer has a sufficient content of hydrophilic groups.

The aqueous polyester dispersion which is used may be an aqueous dispersion of anionic, cationic, non-ionic or amphoteric polyester, of polyesteramides, or of alkyds, i.e. of fatty-chain polyesters, individually or in a mixture. The dispersion may also be a dispersion of polyesters with ionizable side groups, such as sulpho or carboxyl groups. The polyester may contain unsaturated groups, for example when it is obtained by polycondensation of a diol or a diamine with an unsaturated acid anhydride, for example maleic anhydride. In this case the charge of the free-radical monomer may react subsequently with the unsaturated polyester and may give rise to grafting and/or to crosslinking. In this way a dispersion of a grafted and/or crosslinked hybrid polymer is obtained, which may, following application of the dispersion, impart to the film obtained particular mechanical properties, such as an improvement in the adhesion of the said film.

The aqueous dispersion of hybrid polyester polymers according to the invention is obtained by free-radical polymerization of at least one monomer in the interior and/or partially at the surface of already existing polyester particles.

The radical monomer may be vinyl or acrylic in nature and may be anionic, cationic, non-ionic or amphoteric. It is also possible to use a mixture of monomers of different kinds. The monomer or monomer mixture is preferably insoluble or slightly soluble in water. Among the monomers which may be employed, it is possible to mention esters or acrylic or methacrylic acid, such as methyl, ethyl, propyl, butyl, isobutyl, tert-butyl and 2-ethylhexyl acrylate or methacrylate; N-substituted or N,N-substituted acrylamides or methacrylamides; vinyl esters such as vinyl acetate; and styrene. It is also possible to use, individually or in a mixture, a vinyl, acrylic or methacrylic monomer comprising one or more siloxane groups, in particular the monomer of formula

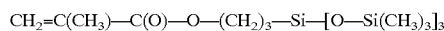

a silicon-containing macromonomer with a monofunctional vinyl, allyl, methacrylic or acrylic acid ester, ether or amide end group, of formula

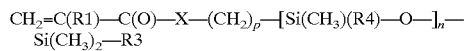

in which R1 represents H or $CH_3$, X represents O or NH, p is an integer which may be zero, R3 and R4 independently represent $CH_3$ or an aliphatic, cycloaliphatic or aromatic group, and n is an integer which is preferably between 3 and 300. It is also possible to use a vinyl or allyl monomer or a methacrylic or acrylic acid ester, ether or amide monomer containing one or more halogenated groups, especially chlorinated and/or fluorinated groups, and/or containing a group which absorbs in UVA and/or UVB and which is able to provide, after polymerization, a certain photoprotection against ultraviolet radiation, especially solar radiation, for example substituted or unsubstituted benzylidenecamphor and benzotriazole groups, among which 2-(2'-hydroxy-5-methacryloyloxyethylphenyl)-2H-benzotriazole may be mentioned.

When the monomer or monomer mixture is in liquid form at room temperature, the free-radical polymerization may be carried out without employing a solvent. When the monomer or monomer mixture is in solid form at room temperature, it may be dissolved before the polymerization, preferably in an organic solvent, for example a polar and water-miscible solvent such as methanol. In this case, after polymerization, it is possible to distill off the organic solvent present in the aqueous dispersion, if necessary.

The aqueous dispersions according to the invention are prepared under conditions such that the monomer polymerizes in the interior and/or partially at the surface of the polymer particles without any nucleation, i.e. without the formation of new particles. To achieve this, the polyester polymer in aqueous dispersion having a solids content of 30–50% by weight may be introduced into a polymerization reactor. It is then possible to add to this reactor the monomer or monomer mixture, as it is or in solution in an appropriate solvent, and a free-radical polymerization initiator.

Depending on what kind it is, the free-radical initiator is introduced in the form of a solution in an organic solvent, in the form of an aqueous solution, or else dissolved beforehand in the monomer mixture. In the first case, it may be added at the same time as the monomer in solution, and in the second case it may be added after the monomer. An organic free-radical polymerization initiator which is not soluble in water may be used, of the peroxide or percarbonate type, such as tert-butyl, peroxy-2-ethylhexanoate, or a water-soluble organic initiator, or else an inorganic initiator such as potassium persulphate.

An aqueous mixture is thus prepared which comprises the polyester polymer, the monomer and the polymerization initiator. It is also possible to add to this mixture a stabilizer which may be, in particular, a surfactant or a mixture of surfactants which is or are anionic, amphoteric, cationic and/or non-ionic. When the polyester used is itself ionic, it is preferred to use a surfactant of the same ionic or amphoteric kind. It is preferred to use an ionic, polyoxyethylenated surfactant in a quantity of 0.5–10% by weight of solids, relative to the weight of polyester solids. The mixture is then heated to the required temperature so as to allow the decomposition of the initiator, and polymerization is continued until the monomers have been consumed.

The proportions of radical monomer to polyester polymer may be 10–95% by weight of radical monomer solids and 5–90% by weight of polyester solids.

An aqueous dispersion of hybrid polymer is thus obtained whose constituent particles are present in the form of composite particles, similar to an "alloy" of the two base polymers and with a size comparable with that of the polyester particles before free-radical polymerization. The dispersions thus obtained possess characteristic properties which are different from those which would be obtained by mixing two aqueous dispersions of each of the constituents.

The dispersions according to the invention may be used as film-forming agent in hair-care compositions such as lacquers or shampoos, hair-setting lotions, styling lotions or mousses, in the same way as an aqueous polymer dispersion according to the state of the art. These compositions comprise the ingredients which are conventionally employed in the hair-care field, and may be prepared according to the usual methods which are known to the person skilled in the art. It is also possible to use the dispersions according to the invention in products which are intended for the photoprotection of hair against ultraviolet radiation, in particular against solar radiation, when they contain an appropriate monomer which is capable of providing a certain sun protection.

The invention is illustrated in greater detail in the examples which follow, in which percentages are given by weight.

EXAMPLE 1

50 g of solid granules of a polyester polymer containing sulpho groups—AQ 38 sold by Eastman Kodak were dispersed in 250 ml of deionized water heated beforehand to 80° C., while maintaining shear stirring with the aid of a Moritz type disperser. A dispersion was obtained which had a mean particle size of 40 nm with a polydispersity of 0.15. The dispersion was left to stand for 24 hours and then introduced into a reactor heated beforehand to 80° C.; 50 g of methyl methacrylate were added dropwise, this addition taking about 45 minutes, and the mixture was then stirred for 1 hour at 80° C. 0.5 ml of tert-butyl peroxy-2-ethylhexanoate (Trigonox 21S from Akzo) was added and the mixture was left to react for 6 hours with stirring and bubbling-in of nitrogen at 80° C.

The resulting mixture had the same appearance as at the beginning, although all of the monomer had polymerized. The temperature of the reaction mixture was reduced to 25° C., the mixture was filtered through a nylon cloth, and the dispersion was concentrated under reduced pressure until a solids content of 40% was obtained. A dispersion was thus obtained which, after a further filtration, had the following characteristics:

mean particle size, determined by a Coulter N4 quasi-elastic light diffusion apparatus from Coultronix: 44 nm
polydispersity: 0.15

Taking into account that the size of the particles in the initial dispersion of polyester AQ 38 was 40 nm (polydispersity 0.15), it was observed that the polymerization of the monomer had virtually no modifying effect on the size of the said initial particles. There was no double distribution of particles, signifying that the polymerization did not lead to the creation of a second population of particles in addition to the initial population.

The dispersion obtained was an aqueous dispersion of a hybrid polymer whose particles resulted from the free-radical polymerization of a methyl methacrylate monomer on and/or in the particles of an existing polymer of the polyester with sulpho groups type.

EXAMPLES 2 TO 5

In a manner similar to that described in Example 1, an aqueous dispersion of granules of a sulpho polyester (AQ 48 from Eastman Kodak) was used to prepare various hybrid polymers according to the table below. Initiation was carried out in each case with 0.5 ml of Trigonox 21S.

The measurements of particle size and of polydispersity were carried out for a dispersion having a solids content of 40%.

|  | polyester | water added | monomer | particle size | polydispersity |
|---|---|---|---|---|---|
| Example 2 | 70 g | 250 ml | 30 g of methyl methacrylate | 35 nm | 0.10 |
| Example 3 | 50 g | 250 ml | 45 g of methyl methacrylate + 5 g of ethylene glycol dimethacrylate | 45 nm | <0.10 |
| Example 4 | 70 g | 250 ml | 30 g of isobutyl methacrylate | 45 nm | 0.12 |
| Example 5 | 70 g | 300 ml | 25 g of methyl methacrylate + 5 g of ethylene glycol dimethacrylate | 32 nm | 0.18 |

It was found that for all these examples a unique and homogeneous population of particles was obtained, whose size had undergone little modification by the polymerization.

EXAMPLE 6

The film-forming properties of polymer dispersions according to the invention was compared at room temperature. It was observed that the dispersions of Examples 1, 2, 3 and 5 formed films when a plasticizer (20 g of tripropylene glycol monomethyl ether per 100 g of dispersion solids) was added to them, making it possible to obtain films which were homogeneous and transparent after drying.

EXAMPLE 7

A fixing spray packaged in a pump bottle was prepared by placing, in an appropriate container:

| aqueous dispersion of Example 1 (40% solids content) | 22.5 g |
| tripropylene glycol monomethyl ether | 18 g |
| fragrance, dye, preservative | q.s |
| water | q.s. 100 g |

After preparation of the mixture, the container was provided with an atomizer pump.

A fixing spray was thus obtained which made it possible to obtain, after spraying on the hair, a film having the appropriate properties.

EXAMPLE 8

A hair-setting lotion was prepared which had the following composition:

| aqueous dispersion of Example 1 (40% solids content) | 25 g |
| fragrance, dye, preservative | q.s. |
| water | q.s. 100 g |

A hair-setting lotion was thus obtained which made it possible to obtain, after application to the hair, a film having the appropriate properties.

EXAMPLE 9

Similarly to Example 8, a hair-setting lotion was prepared which comprised an aqueous dispersion as prepared in Examples 2 to 5 diluted to a solids content of 5% by weight. In all four cases a lotion was obtained which enabled the hairstyle to be fixed well.

EXAMPLE 10

2.5 g of solid granules of a polyester polymer containing sulpho groups—AQ 38 sold by Eastman Kodak were dispersed in 200 ml of deionized water heated beforehand to 80° C., while maintaining shear stirring with the aid of a Moritz type disperser. 1 g of sodium lauryl sulphate and 0.25 g of potassium persulphate were added. The mixture was stirred and then heated to 72° C., and 47.5 g of tert-butyl acrylate were introduced. The mixture was stirred for 8 hours at 72° C. The temperature of the reaction mixture was reduced to 25° C., it was filtered through a nylon cloth, and the dispersion was concentrated under reduced pressure until a solids content of 20% was obtained. A dispersion was thus obtained which had the following characteristics:

mean particle size, determined by a Coulter N4 quasi-elastic light diffusion apparatus from Coultronix: 57 nm polydispersity: 0.15

EXAMPLE 11

A hair-setting lotion was prepared which had the following composition:

| aqueous dispersion of Example 10 (5% solids content) | 25 g |
| fragrance, dye, preservative | q.s. |
| water | q.s. 100 g |

A hair-setting lotion was thus obtained which enabled the hairstyle to be fixed well.

EXAMPLE 12

An aqueous dispersion of 2.5 grams of polyester polymer containing sulpho groups, AQ 38 sold by Eastman Kodak, was prepared in 200 ml of deionized water and introduced into a reactor heated beforehand to 80° C. 2.5 grams of sodium lauryl sulfate were added, followed by addition of 0.25 grams of potassium persulfate and 0.25 grams of sodium hydrogencarbonate.

The mixture was heated to 72° C., and then a mixture of 42.75 grams of tertbuylyacrylate was added together with 4.75 grams of silicon macromonomer sold by 3M (molecular weight 9,000 to 12,000).

The mixture was maintained at 72° C. under stirring for 24 hours; then the temperature of the reaction mixture was lowered to 25° C. The mixture was then filtered by means of a nylon cloth, and the dispersion, under reduced pressure, was then concentrated to obtain a ratio of 20% solids content.

The dispersion obtained was an aqueous dispersion of a hybrid polymer wherein silicone macromonomer and tert-butylacrylate monomers were polymerized within and/or partially at the surface of the preexisting particles of polymer of the polyester polymer containing sulpho groups.

EXAMPLE 13

A hair-setting lotion was prepared which had the following composition:

| aqueous dispersion of example 12 (5% solids content) | 25 g |
| fragrance, dye, preservative | q.s. |
| water | q.s. to obtain 100 g |

A hair-setting lotion was thus obtained which enabled the hairstyle to be well fixed.

EXAMPLE 14

An aqueous dispersion of 2.5 grams of polyester polymer containing sulpho groups, AQ 38 sold by Eastman Kodak, was prepared in 200 ml of deionized water and introduced into a reactor heated beforehand to 80° C. 2.5 grams of sodium lauryl sulfate were added, followed by addition of 0.25 grams of potassium persulfate and 0.25 grams of sodium hydrogencarbonate.

The mixture was heated to 72° C., and then a mixture of 42.75 grams of tertbuylyacrylate was added together with 4.75 grams of perfluorohexyl acrylate (ATOCHEM).

The mixture was maintained at 72° C. under stirring for 24 hours; then the temperature of the reaction mixture was lowered to 25° C. The mixture was then filtered by means of a nylon cloth, and the dispersion, under reduced pressure, was then concentrated to obtain a ratio of 20% solids content.

The dispersion obtained was an aqueous dispersion of a hybrid polymer wherein perfluorohexyl acrylate and tertbutylacrylate monomers were polymerized within and/or partially at the surface of the preexisting particles of polymer of the polyester polymer containing sulpho groups.

EXAMPLE 15

A hair-setting lotion was prepared which had the following composition:

| | |
|---|---|
| aqueous dispersion of example 14 (5% solids content) | 25 g |
| fragrance, dye, preservative | q.s. |
| water | q.s. to obtain 100 g |

A hair-setting lotion was thus obtained which enabled the hairstyle to be well fixed.

What is claimed is:

1. A hair-care composition, which comprises an aqueous polymeric dispersion comprising particles composed of hybrid polymers resulting from the free-radical polymerization of:
   at least one radical monomer selected from vinyl compounds and acrylic compounds with
   particles of at least one polymer selected from polyesters, polyesteramides, and alkyds,
   wherein said monomer is polymerized within and/or at the surface of said polymer particles and is present in an amount ranging from about 5–90% by weight, and wherein said polymer is present in an amount ranging from about 10–90% by weight.

2. A method of forming a film in a hair care composition, comprising forming said film with an effective amount of an aqueous polymeric dispersion comprising particles composed of hybrid polymers resulting from the free-radical polymerization of
   at least one radical monomer selected from vinyl compounds and acrylic compounds with
   particles of at least one polymer selected from polyesters, polyesteramides, and alkyds,
   wherein said monomer is polymerized within and/or at the surface of the particles of said polymer and is present in an amount ranging from about 5–90% by weight, and wherein said polymer is present in an amount ranging from about 10–90% by weight.

3. The composition of claim 1, wherein the radical monomer is chosen from esters of acrylic and methacrylic acids; N-substituted and N,N-substituted acrylamides and methacrylamides; vinyl esters; styrene; vinyl, acrylic and methacrylic monomers comprising one or more siloxane groups; vinyl and allyl monomers and acrylic and methacrylic acid ester, ether or amide monomers containing at least one group selected from halogenated groups and from groups capable of absorbing in at least one region selected from the UVA region and the UVB region and being able to provide, after polymerization, photoprotection against ultraviolet radiation.

4. The composition of claim 3, wherein the halogenated groups are selected from chlorinated and fluorinated groups.

5. The composition of claim 3, wherein the group capable of absorbing in at least one region selected from the UVA and the UVB region is a substituted or unsubstituted group selected from benzylidenecamphor and benzotriazole.

6. The composition of claim 5, wherein the benzotriazole group is 2-(2'-hydroxy-5-methacryloyloxyethylphenyl)-2H-benzotriazole.

7. The composition of claim 3, wherein the siloxane group is the monomer of formula

a silicon-containing macromonomer with a monofunctional vinyl, allyl, methacrylic or acrylic acid ester, ether or amide end group of formula

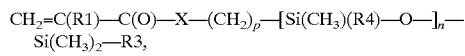

in which R1 represents H or $CH_3$, X represents O or NH, p is an integer which may be zero, R3 and R4 independently represent an aliphatic, cycloaliphatic or aromatic group, and n is an integer.

8. The composition of claim 7, wherein n is an integer of from 3 to 300.

9. The composition of claim 1, wherein said at least one polymer is an anionic, cationic, nonionic or amphoteric polyester, a polyester with ionizable side groups, a polyester containing unsaturated groups, or mixtures thereof.

10. The composition of claim 9, wherein the ionizable side groups are selected from sulpho and carboxyl groups.

11. A composition in the form of an aerosol lacquer, a shampoo, a hair-setting lotion, a styling lotion or a styling mousse, which comprises an effective amount of a composition of claim 1 in said lacquer, shampoo, lotion, or mousse.

12. A composition for the photoprotection of hair against ultraviolet radiation, which comprises an effective amount of a composition of claim 1.

13. The composition of claim 7, wherein said aliphatic group of $R_3$ and $R_4$ is $CH_3$.

14. The method of claim 2, wherein the hair-care composition is an aerosol lacquer, a shampoo, a hair-setting lotion, a styling lotion, or a styling mousse.

15. The method of claim 2, wherein the hair-care composition is a product for the photoprotection of hair against ultraviolet radiation.

16. The method of claim 15, wherein the ultraviolet radiation is solar radiation.

17. The composition of claim 12, wherein the ultraviolet radiation is solar radiation.

* * * * *